United States Patent [19]

Price

[11] 4,008,131
[45] Feb. 15, 1977

[54] PURIFICATION OF ACETIC ACID

[75] Inventor: Jerry L. Price, Texas City, Tex.

[73] Assignee: Monsanto Company, St. Louis, Mo.

[22] Filed: Dec. 11, 1975

[21] Appl. No.: 639,668

[52] U.S. Cl. .................................. 203/82; 203/16; 203/98; 203/99; 203/DIG. 19; 260/541

[51] Int. Cl.$^2$ .................... B01D 3/14; C07C 51/44

[58] Field of Search ........ 203/16, 4, 14, 15, 17–19, 203/98, 99, 82, 84, 78, 75; 260/541

[56] References Cited

UNITED STATES PATENTS

| | | | |
|---|---|---|---|
| 2,412,215 | 10/1946 | Guinot | 260/541 |
| 2,854,385 | 9/1958 | Alheritiere | 203/16 |
| 3,073,752 | 1/1963 | Mention | 203/82 |
| 3,210,271 | 10/1965 | Byerly et al. | 203/82 |
| 3,769,177 | 10/1973 | Eubanks et al. | 260/541 |
| 3,791,935 | 2/1974 | Eubanks et al. | 260/541 |

Primary Examiner—Wilbur L. Bascomb, Jr.
Attorney, Agent, or Firm—Elizabeth F. Sporar

[57] ABSTRACT

A method is provided for removal of excess water which tends to build up in recycle streams and reduces the rate of pure acid production during operation of a distillation system for purification of crude acetic acid containing water and methyl iodide. The crude acid is introduced into the upper half of a distillation zone. The methyl iodide, a major proportion of water and an equivalent amount of acid are removed overhead from the zone. A minor proportion of the water containing a small amount of acetic acid is removed as a liquid sidedraw at a point near the top of the distillation zone. A product acid stream essentially dry and substantially free of methyl iodide is removed from the bottom of the distillation zone. The overhead stream can be stored, disposed of or preferably recycled to the acid-producing step. The liquid water sidedraw may either be discarded or subjected to rectification for recovery of acid values.

9 Claims, 1 Drawing Figure

PURIFICATION OF ACETIC ACID

BACKGROUND OF THE INVENTION

The present invention relates to the purification of acetic acid. More particularly, it relates to the removal of water from acetic acid streams produced using a catalytic system containing an iodine component.

A process has recently been developed for the production of carboxylic acids such as acetic acid by the reaction of an alcohol or an ester, or ether and halide derivatives thereof, with carbon monoxide in contact with catalyst systems formed on mixing of a rhodium or iridium component and a halogen component in the presence of carbon monoxide (U.S. pat. Nos. 3,769,329 and 3,772,380). In actual practice, the halogen component is generally iodine in the form of an alkyl iodide, notably methyl iodide, or hydrogen iodide. The acid product thus produced contains water and residual amounts of the iodine component as contaminants. In order that the acid produced in such a process can be employed in further reactions and other uses, it must be freed from any water present as well as from the small amounts of iodine present. The usual methods of purification to recover the acetic acid and removal of the halogen contaminants involves a series of distillations. Water can be removed, for example, by the distillation techniques described in U.S. Pat. No. 3,769,177 and 3,791,935. However, it has been found that water cannot be removed by these methods without simultaneous removal of the alkyl iodide such as methyl iodide because methyl iodide does not remain in the liquid phase, either in acetic acid or water, and is taken overhead with the water. Since economics dictate that the methyl iodide must be reused, the water-methyl iodide stream is generally recycled to the reactor. Also, water removal at the levels indicated requires acid removal as well, the acid/water weight ratio being about 1:1. It is obvious, of course, that this stream also has to be recycled to recover the acid values. This operation is satisfactory until water buildup in the system due to lack of reaction as well as leaks result in excess amounts of water in the feed to the drying column which create a bottleneck in the drying operation forcing a cutback in rates which considerably slows down production of pure acid. One obvious corrective action to reduce the water content of the feed would be to discard water from the overhead stream. Discarding water also means discarding methyl iodide, however, and creates a disposal problem in addition to the adverse economic effect resulting when methyl iodide is not recycled. It is, accordingly, an object of the present invention to provide a method for the removal of excess water during distillation of a crude acetic acid product to remove water and methyl iodide therefrom which does not result in any loss of methyl iodide or create any disposal problems and wherein the amount of acetic acid simultaneously removed is such that the resulting acid-water stream can be disposed of or rectified at low cost as desired.

SUMMARY OF THE INVENTION

According to the purification process of the present invention, a stream of acetic acid containing as contaminants water and methyl iodide is introduced into the upper half of a distillation zone. The methyl iodide is removed overhead from the distillation zone together with a major portion of the water and an equivalent amount of acid, a portion of said overhead stream being returned as reflux to the top of the zone. A minor portion of the water containing some acetic acid but no methyl iodide is removed as a liquid side-draw at a point near the top of said zone which is above the point of introduction of the feed to said zone. An acetic acid stream essentially dry and substantially free of methyl iodide is removed at or near the bottom of said distillation zone. The acid contained in the liquid sidedraw stream removed from near the top of the zone can be removed by feeding said stream into the bottom of a rectification zone, removing water overhead, condensing said water and discarding the major portion thereof while returning a minor portion thereof as reflux to said rectification zone, removing acid from the bottom of said rectification zone and recycling said acid to the distillation zone at a point in the upper section thereof. Alternatively, the liquid sidedraw can be discarded if acid recovery is not deemed desirable.

DESCRIPTION OF THE PREFERRED EMBODIMENTS

Figure 1:
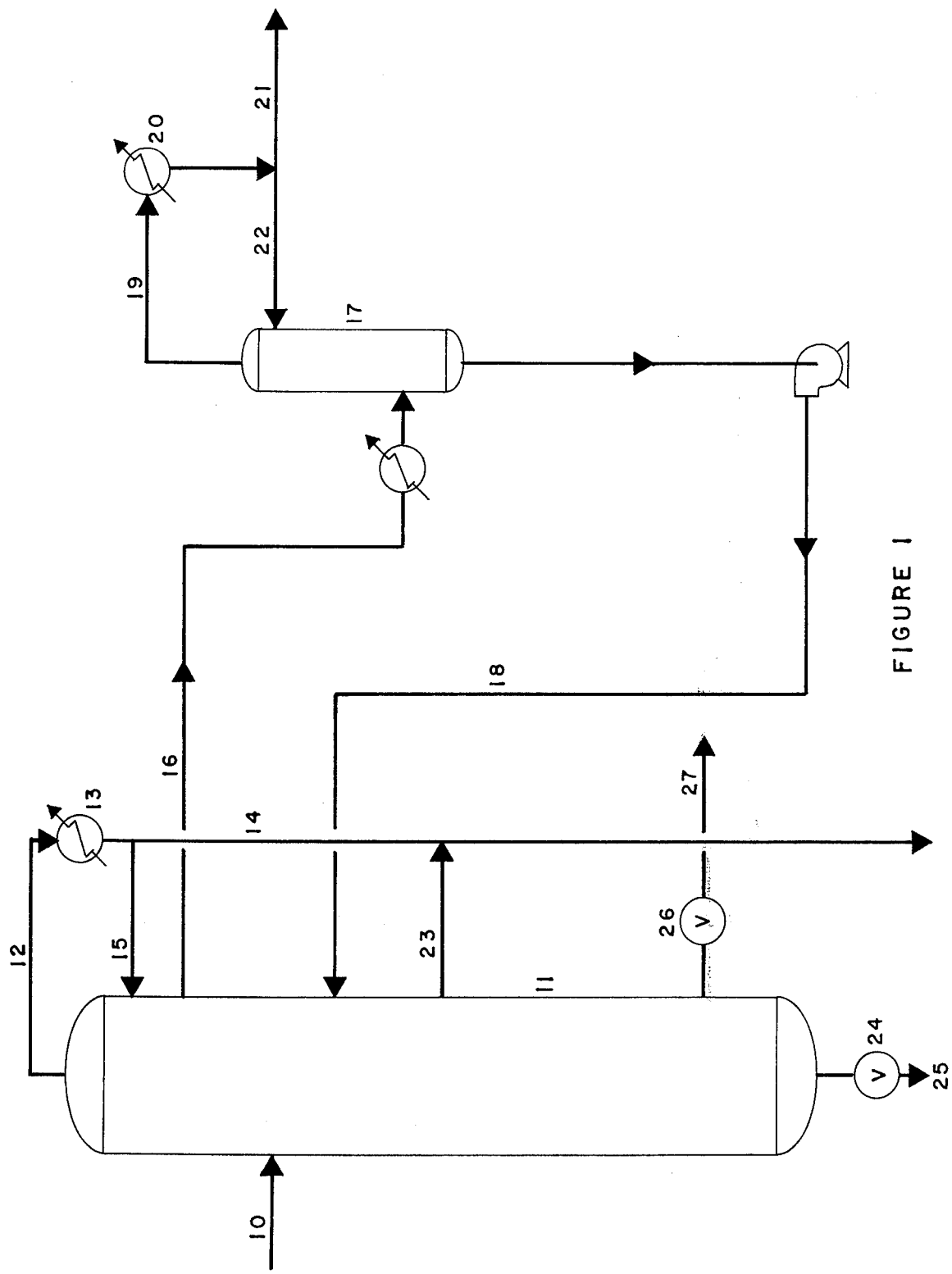
FIG. 1 is a schematic flow diagram of one specific embodiment of the purification process of the invention.

The process of the invention will be more clearly understood from the following description of one specific embodiment thereof with reference to the process flow diagram in FIG. 1. The acetic acid stream to be purified is introduced via line 10 into distillation column 11 in the upper half thereof. This acid stream contains in addition to acetic acid a substantial proportion of water and methyl iodide and usually a relatively small proportion of hydrogen iodide. In some instances there will also be present, trace amounts of metallic halides. An overhead stream is removed via line 12 and condensed in condenser 13, the condensed stream passing via line 14 to either storage or recycle to the preceding acid-producing step or process. A portion of the overhead is recycled via line 15 to serve as reflux in the column. This overhead stream comprises essentially all of the methyl iodide contained in the feed along with a major proportion of water, and some of the acid but essentially none of the hydrogen iodide contained therein. A liquid stream is removed from the side of the column near the top via line 16 which comprises a minor proportion of the water contained in the feed, a minor proportion of acid and essentially no methyl iodide or hydrogen iodide. This stream is introduced into the bottom of column 17 wherein the acid is separated as the bottoms stream, this stream being returned via line 18 to column 11. The overhead from column 17 consisting essentially of water is withdrawn via line 19, condensed in condenser 20 and discarded via line 21, a small amount of the condensate being returned through line 22 as reflux to column 17. If desired, liquid sidedraw 16 need not be subjected to rectification but may be discarded without regard to recovery of the acid if the amount of acid contained therein does not warrant the extra processing step.

If, as is the case in the present example, the feed stream also contains a small amount of hydrogen iodide, the removal of the hydrogen iodide can be accomplished in any of several different ways and the manner in which it is removed constitutes no part of the present invention. For purposes of illustration only, the method of removal of hydrogen iodide shown in FIG. 1 is that described and claimed in U.S. Pat. No. 3,791,935. A stream is withdrawn from the middle portion of the distillation column 11 via line 23 at or near the peak concentration of hydrogen iodide in the acetic acid-water mixture. This sidestream withdrawn via line 23 is monitored and controlled as to its temperature thus determining the percentage of water in the sidestream composition. This control serves to insure that the sidestream is taken from near the peak of concentration of hydrogen iodide in column 11. The temperature of the sidestream is monitored and controlled by increasing or decreasing the heat added in the reboiler portion of the column as a result of such measurement. This sidestream is either directed to waste, to storage or preferably is recycled to the prior acid production step via line 14.

As a result of the treatment and distillation in column 11, a purified acetic acid stream is withdrawn at either of two alternative points in column 11. When there are little or no metallic impurities present, the purified acetic acid is withdrawn directly from the bottom of column 11 via valve 24 and line 25 since this bottoms product will have the lowest water and hydrogen iodide content. If any significant amount of metallic halides are present in the system, then these will collect in the reboiler of column 11 and in order to recover an acetic acid stream free from such metallic impurities, the product acetic acid stream is removed in the form of a vapor just above the liquid level maintained in the reboiler. This sidestream is removed just above the lowest plate in the distillation column via valve 26 and line 27. In this latter preferred mode of withdrawal of the purified acid stream, any metal halides which have collected in the sump in the reboiler of column 11 can be withdrawn via valve 24 and line 25 at intervals and that acid stream containing metallic halides can either be discarded, stored or preferably returned to the prior production process. The product acid stream recovered in either of the alternative methods via line 25 or line 27 is essentially dry acetic acid substantially free of both methyl iodide and hydrogen iodide present in the original crude acid charged to the system via line 10.

An alternative method to that described above for removal of HI involves introduction of methanol into the lower section of the distillation zone as disclosed and claimed in application Ser. No. 603,825 filed Aug. 11, 1975 in which case the sidedraw of HI via line 23 in FIG. 1 is eliminated and the methyl acetate generated by the methanol addition and any excess methanol is removed overhead from the column 11 with the methyl iodide and water. This overhead stream is, of course, also suitable for recycle to the acid-producing step. In another alternative method, HI can be removed from the bottom of the column together with the acid and the two compounds separated by further distillation. Other methods will be obvious to those skilled in the art.

In the purification process briefly described above and illustrated in FIG. 1, the distillation zone can comprise any distillation column normally used for separation and purification and can be either the packed or plate type or can be a combination packed-plate type. Generally, the distillation column will be of the plate-type having from 20 to 100 trays and preferably from 30 to 80 trays. Although bubble-cap trays and ballast trays may be employed in the column constituting the main distillation zone, sieve trays are preferred.

Similarly, the rectification zone can comprise any distillation column normally employed for separation of fluids and it can also be of the packed or plate type or a combination of packed-plate type. Generally, where rectification of the liquid sidedraw is effected as shown in FIG. 1, the rectification zone as represented by column 17 will comprise a packed column having from two to 20 theoretical trays, and preferably from about four to about 10 theoretical trays.

The associated condensers employed with one or both columns as described are of generally conventional design and manufacture. As will be recognized, various pumps, compressors, reboilers, separation vessels, etc., normally employed in carrying out chemical purification processes can be employed in the process described herein. Since these are no part of the invention, details of their use in various phases of the process description have not been included.

Temperatures and pressures employed in the distillation zone, and the rectification zone when one is used, can vary. As a practical matter, these zones are most often operated at pressures from approximately atmospheric to about 10 kg/cm$^2$. Within this range, pressures from atmospheric to 5.25 kg/cm$^2$ are usually used and those within the range from atmospheric to 3.8 kg/cm$^2$ are preferred. Temperatures within the zones will normally lie between approximately the boiling point of water and at or slightly above the boiling point of the acetic acid being purified at the pressure in the zone. At the usual or preferred pressures, the bottoms temperature of the zone or zones generally will be in the range of from approximately the boiling point of the acid-water mixtures at the pressure employed to as high as 165° C or higher, but preferably maintained around 155° C. The temperature at the top of the zones likewise can range from as low as 100° C up to the boiling point of the acid being purified at the pressure employed. When employing both distillation and rectification zones, the temperatures and pressures in the two zones may be the same or different so long as both are within the ranges set forth above.

The feed stream to the distillation zone can be introduced anywhere in the upper half of that zone. Generally, this feed is introduced at a point above two-thirds of the height of that distillation zone or into the upper one-third thereof. The liquid sidestream containing a high percentage of water is taken from the upper part of the distillation zone at some level above the level of the introduction of the feed to the distillation zone. Generally, this liquid sidedraw will be taken from the upper one-fourth of the distillation zone and preferably from the upper one-tenth thereof. The quantity of water removed via the liquid sidedraw is not critical except insofar as column size considerations and the time in which it is desired to reduce the amount of water being withdrawn from the column for storage or recycle are concerned. In practical operation, from about 10 to about 20% of the total water in the overhead stream withdrawn from the column for storage or recycle is removed via the liquid sidedraw depending upon how rapidly removal of excess water in the system is required.

The liquid sidedraw stream can be discarded if desired or, depending upon its acid content, can be processed as shown in FIG. 1 to recover acid values therefrom. In the latter case, the liquid sidedraw stream is introduced into the lower half of a rectification zone and preferably into the lower one-tenth of such a zone.

The separation in said zone is conventional and straightforward with water being removed overhead and discarded and the acid bottoms stream being recycled to the distillation zone below the liquid sidedraw.

The product stream removed from the distillation zone can be removed at any point in the lower one-third and preferably from the lower one-tenth of this zone. As previously discussed above, the preferred point for withdrawal is to take the vapor just above or below the lowest plate in the column in the event that metallic halides are present. When corrosion products are not present in the column as when they have been removed by a prior distillation step, the most desirable point for withdrawal of the dried and purified acetic acid is as the bottoms stream from the distillation zone.

The The following example is presented to illustrate the invention but is not to be construed as limiting it in any manner whatsoever.

EXAMPLE

The effluent from the reaction of methanol and carbon monoxide in contact with a catalyst system comprising rhodium iodide and methyl iodide is passed to a separation zone wherein the carbonylation products are flashed overhead from the liquid reaction mass. The overhead stream comprising acetic acid, water, hydrogen iodide and methyl iodide is dried and purified of iodine components in a distillation recovery system such as that described and illustrated in FIG. 1 of U.S. Pat. No. 3,791,935. The acetic acid-water stream is fed to the 33rd plate of a 50-plate distillation column and purified in a continuous process wherein a sidestream is withdrawn from the 19th plate of such column and returned to the flash separation step and a purified product stream is withdrawn from the bottoms of the distillation column. Typical operating data for this system are presented in Section A of Table 1 below.

After operation over a period of time in the fashion described above, water balance is such that the feed to the column must be reduced 1% in 1 hour. The column is modified to provide for operation as shown in FIG. 1 attached with a liquid stream being withdrawn from the 45th plate and operated continuously over a period of 1 hour with this arrangement, the liquid stream withdrawn being discarded to waste. Operating data for this period are presented in Section B of Table 1.

At the end of the one-hour period, the liquid sidedraw is discontinued and the column returned to the operation as described above with reference to Section A. Data for this period of operation are presented in Section C of Table 1. The operating data over the indicated periods of time demonstrate that at the same production rate (acetic acid in bottoms stream), the distillation column is handling only 97% of the original feed after operating with the liquid water sidedraw near the top of the column. It is thus evident that the process of the invention provides a means to correct water build-up in the purification system. The required separation is still attained but the load on the column can be reduced by using the liquid sidedraw to remove water from the column.

TABLE 1

| A. Operating without liquid sidedraw of $H_2O$ | | | | |
|---|---|---|---|---|
| LB/HR | FEED | OVERHEAD | BOTTOMS | SIDEDRAW |
| Water | 15 | 14.9 | 0.1 | 0 |
| Acetic Acid | 84.7 | 14.8 | 69.9 | 0 |
| MeI | 0.3 | 0.3 | 0 | 0 |
| TOTAL | 100 | 30 | 70 | 0 |

TABLE 1-continued

| B. Sidedraw on at time 0 | | | | |
|---|---|---|---|---|
| Water | 15 | 13.5 | 0.1 | 1.4 |
| Acetic Acid | 84.7 | 14.8 | 66.7 | 3.2 |
| MeI | 0.3 | 0.3 | | 0 |
| TOTAL | 100 | 28.6 | 66.8 | 4.6 |
| C. Sidedraw Discontinued after 1 hour | | | | |
| LB/HR | FEED | OVERHEAD | BOTTOMS | SIDEDRAW |
| Water | 13.6 | 13.5 | 0.1 | 0 |
| Acetic Acid | 83.1 | 13.2 | 69.9 | 0 |
| MeI | 0.3 | 0.3 | | 0 |
| TOTAL | 97.0 | 27.0 | 70.0 | 0 |

The process of the present invention is particularly applicable for employment on an intermittent basis in conjunction with a process for purifying acetic acid such as that disclosed and claimed in U.S. Pat. No. 3,791,935 or in application Ser. No. 603,825 filed Aug. 11, 1975. At such times, during the purification of acetic acid according to these processes when excessive water builds up in the system, the process described and claimed herein can be employed to reduce the water to the desired level. Only minor modifications are required, for example, to the distillation column used in either of these processes to make it adaptable for operation according to the process of the present invention, namely, provision for removal of a liquid sidedraw at a point in the upper section of the column. However, the method described herein for removal of excess water is also applicable to other purification systems wherein HI is removed in other ways.

What is claimed is:

1. A process for the purification of acetic acid streams containing water and methyl iodide as contaminants which comprises:
    a. introducing an acetic acid stream containing water and said methyl iodide contaminant into the upper half of a distillation zone, and
    b. removing an overhead fraction containing substantially all of the methyl iodide, a major amount of water and a minor amount of acetic acid charged to said zone, and
    c. removing a liquid sidestream containing a minor amount of the water charged to said zone containing some acetic acid but no methyl iodide at a point in the upper one-fourth of said distillation zone, and
    d. removing from the lower part of said zone acetic acid which is substantially dry and free of methyl iodide.

2. The process of claim 1 wherein said liquid sidedraw is removed from the upper one-tenth of said distillation column.

3. The process of claim 2 wherein the amount of water removed via the liquid sidedraw in (c) is from about 10% to about 20% of the water in the overhead stream withdrawn from the column for storage or recycle.

4. The process of claim 1 wherein said distillation zone comprises a distillation column having 20 to 100 trays.

5. The process of claim 1 wherein the distillation zone is maintained at a pressure from atmospheric to 3.8 kg/cm$^2$ and at temperatures of from 100° to 165° C.

6. The process of claim 1 wherein said liquid sidedraw from (c) is introduced into the lower part of a rectification zone, water is removed as an overhead fraction from said rectification zone, condensed and a portion thereof is returned to said rectification zone as reflux, and acid is removed as a bottoms stream from said rectification zone.

7. The process of claim 6 wherein said rectification zone comprises a distillation column having four to 10 theoretical trays.

8. The process of claim 7 wherein said rectification zone is maintained at a pressure from atmospheric to 3.8 kg/cm$^2$ and at temperatures of from 100° to 165° C.

9. The process of claim 8 wherein said acid bottoms stream from said rectification zone is recycled to the upper section of said distillation zone.

* * * * *